United States Patent
Lerner et al.

(10) Patent No.: US 8,663,703 B2
(45) Date of Patent: Mar. 4, 2014

(54) DRUG MICROPARTICLES, PROCESSES OF PREPARING THEM AND A DRUG DELIVERY VEHICLE COMPRISING THEM

(75) Inventors: E. Itzhak Lerner, Petach Tikva (IL); Vered Rosenberger, Jerusalem (IL); Moshe Flashner-Barak, Petach Tikva (IL); Anna Drabkin, Tzur Hadassah (IL); Naomi Moldavski, Jerusalem (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 357 days.

(21) Appl. No.: 12/635,417

(22) Filed: Dec. 10, 2009

(65) Prior Publication Data

US 2010/0092568 A1  Apr. 15, 2010

Related U.S. Application Data

(62) Division of application No. 10/400,100, filed on Mar. 25, 2003, now abandoned.

(60) Provisional application No. 60/367,957, filed on Mar. 26, 2002.

(51) Int. Cl.
*A61K 9/14*  (2006.01)

(52) U.S. Cl.
USPC ............ 424/493; 424/490; 424/494

(58) Field of Classification Search
None
See application file for complete search history.

(56) References Cited

U.S. PATENT DOCUMENTS 6,074,670 A  *  6/2000  Stamm et al. ............ 424/462
6,761,910 B1 *  7/2004  Pettersson et al. ........ 424/489

* cited by examiner

*Primary Examiner* — Carlos Azpuru
(74) *Attorney, Agent, or Firm* — Baker & Hostetler LLP

(57) ABSTRACT

Provided are microparticles of active pharmaceutical ingredients, which are prepared by removing a sublimable carrier from a solid solution of the a active pharmaceutical ingredients in the sublimable carrier. Also provided are drug delivery vehicles comprising a carrier particle bearing the microparticles on its surface.

8 Claims, No Drawings

DRUG MICROPARTICLES, PROCESSES OF PREPARING THEM AND A DRUG DELIVERY VEHICLE COMPRISING THEM

RELATED APPLICATIONS

This is a divisional patent application of U.S. patent application Ser. No. 10/400,100, filed Mar. 25, 2003 now abandoned, which claims the benefit of U.S. Provisional Patent Application No. 60/367,957, filed Mar. 26, 2002, the disclosures of which applications are hereby incorporated by reference.

FIELD OF THE INVENTION

The present invention relates to microparticles of drugs, especially drugs that are poorly soluble in water, and to methods for making them.

BACKGROUND OF THE INVENTION

Many important drugs have poor oral bioavailability because they are poorly soluble in water. Many approaches have been suggested to overcome this problem. Although some approaches have been used, with limited commercial success, each approach has its own drawbacks and limitations.

In one approach, a water-soluble prodrug of a poorly water-soluble drug is made [1-4]. The prodrug approach is limited to those molecules that have functionality amenable to facile removal in the body to form the drug. Not all poorly water-soluble drugs are so endowed. Furthermore, the prodrug would likely be considered a new chemical entity and require separate approval from regulatory agencies, adding considerable time and cost to bringing the product to market.

The bioavailability of poorly water-soluble drugs has been improved by decreasing the particle size of the drug to increase the surface area. Milling [5-6], high pressure homogenization [7-8], spray drying [9], lyophilization of solutions in water organic solvent mixtures [10], and lyophilization of solutions inorganic solvents [11-12] have been tried. Size reduction is, in principal, generally applicable for improving bioavailability, but achieving size reduction by, for example, high energy milling, requires special equipment and is not always applicable. High pressure homogenization requires special equipment and requires organic solvents that can remain in the comminuted product. Spray drying also requires solvents and generally produces particles that are too large.

Lyophilization is usually limited to materials that are soluble in water in any event, although there have been some efforts at using organic solvents.

The solubility of poorly soluble antibiotics has been improved by complexation with polymers or cyclodextrins. Polymer complexes have been formed with PVP in organic solvent [13a], or with PVP in heated water [13]. Other drugs have been complexed with cyclodextrins and polymers [14-15].

The bioavailability of poorly soluble drugs has been improved by dispersing the drug in a soluble polymer, often with addition of surfactants [16-24].

Some combinations of techniques have shown added improvement. For example spraying and drying a dispersion of drug and polymer or cyclodextrin on pellets in a fluidized bed dried [25-26]. The combination of solid dispersion and lyophilization to improve solubility has been demonstrated [27], and the use of solid dispersions absorbed on a carrier having a large surface area has also been demonstrated [28].

Clearly, there is a need for a simpler and generally applicable means of making and delivering particles of drugs having a size below 10 μm and especially below 1 μm.

Many of the above-described techniques require forming particles by solvent removal which, in turn, entails concentration of a solution. During solution concentration, solute molecules, which in solution are statistically separated into individual molecules and small clusters or aggregates, are drawn together to form larger molecular aggregates. When the solute drug eventually precipitates, relatively larger crystals are formed.

Lyophilization (freeze drying) has the advantage of allowing the solvent to be removed whilst keeping the solute relatively immobile, thereby suppressing enlargement of clusters or aggregates. When the solvent is removed, the formed crystals are smaller or the material is amorphous, reflecting the separation of the molecules in the frozen solution state. Molecular separation can be improved and aggregate formation still further suppressed by lyophilizing a more dilute solution, although one pays a hefty price in energy requirements for removing more solvent. Lyophilization is usually a very slow, energy intensive process and usually requires high vacuum equipment. Furthermore, there is a tendency for the crystals formed to aggregate in the free state, undoing the job that the freeze drying did. This tendency can sometimes be overcome with additives, but these must be compatible with the entire system.

Amorphous or nanoparticulate materials tend to show poor bulk flow properties as powders, requiring formulation work to be able to fill them into capsules. While these problems are not insurmountable, they add further limitations in the usefulness of the system. Many of the existing limitations are overcome by the present invention.

SUMMARY OF THE INVENTION

The present invention relates to a drug delivery vehicle including a pharmaceutical carrier particle, especially a pharmaceutical carrier particle that is a sugar particle, a starch particle, a lactose particle, or a particle of microcrystalline cellulose, bearing microparticles of a drug, especially a drug having poor solubility in water, wherein the microparticles of the drug are deposited on the pharmaceutical carrier particle from a solid solution of the drug in a sublimable carrier such as menthol, thymol, camphor, t-butanol, trichloro-t-butanol, imidazole, coumarin, acetic acid (glacial), dimethylsulfone, urea, vanillin, camphene, salicylamide, and 2-aminopyridine. The drug delivery vehicle of the present invention is useful for delivering a drug, especially a drug that has poor solubility in water, to a mammal, especially a human, in need of treatment with that drug.

In another aspect, the present invention relates to a method of making a microparticle including the steps of forming a solid solution of the drug in a sublimable carrier and removing the sublimable carrier from the solid solution by, for example, sublimation. Sublimation can be accomplished in a fluidized bed apparatus.

In another aspect, the present invention relates to a method of making a drug delivery vehicle including the steps of forming a solid solution of the drug and a sublimable carrier on the surface of a pharmaceutical carrier particle, especially a pharmaceutical carrier particle that is a sugar particle, a starch particle, a lactose particle, or a particle of microcrystalline cellulose, and removing the sublimable carrier from the solid solution, for example by sublimation, to deposit microparticles of the drug on the pharmaceutical carrier particle. The solid solution can be formed on the carrier particle by, for example, combining drug, sublimable carrier, and a solvent (for example ethanol), applying the combination to the carrier particle, and removing the solvent. The solid solution can also be formed by applying a combination of drug and molten sublimable carrier to the particle and allowing the combination to cool to form the solid solution on the carrier particle.

In yet another aspect, the present invention relates to pharmaceutical compositions that include microparticles of the present invention, which microparticles can be born by a drug delivery vehicle of the present invention.

DETAILED DESCRIPTION OF THE INVENTION

The present invention provides microparticles of a pharmacologically active substance, i.e. a drug, and a method for making them. The invention also provides a drug delivery vehicle for administering a pharmacologically active substance, and methods for making it, wherein the delivery vehicle includes at least one pharmaceutical carrier particle bearing microparticles of the drug, which microparticles are made according to the present invention.

Microparticles of the present invention are formed as described hereinbelow and generally have mean dimensions on the order of about 100 nm, up to about 10 µm. Microparticles according to the present invention can have a regular shape, e.g. essentially spherical, or they can have an irregular shape. The material of which microparticles are comprised can be crystalline or it can be at least partly amorphous. Preferably the material is at least partly amorphous.

As used herein in connection with a measured quantity, the term about refers to the normal variation in that measured quantity that would be expected by the skilled artisan making the measurement and exercising a level of care commensurate with the objective of the measurement and the precision of the measuring equipment used.

Any pharmacologically active substance (drug) can be used in the practice of the present invention. However, drugs having poor water solubility (poorly water soluble drugs), and hence relatively lower bioavailability, are preferred and the advantages of the present invention are more fully realized with poorly water-soluble drugs. For purposes of the present invention, a drug is considered to be poorly water soluble if it has a solubility of less than about 20 mg/per milliliter of water. Examples of drugs having poor water solubility include fenofibrate, itraconazole, bromocriptine, carbamazepine, diazepam, paclitaxel, etoposide, camptothecin, danazole, progesterone, nitrofurantoin, estradiol, estrone, oxfendazole, proquazone, ketoprofen, nifedipine, verapamil, and glyburide, to mention just a few. The skilled artisan knows other drugs having poor water solubility.

Pharmaceutical carrier particles useful for making the delivery vehicle of the present invention are made of comestible substances and are well known in the art. Examples of useful pharmaceutical carrier particles include particles, that can be non-pariel pellets, typically between about 0.1 mm. and about 2 mm. in diameter, and made of, for example, starch, particles of microcrystalline cellulose, lactose particles or, particularly, sugar particles. Suitable sugar particles (pellets, e.g. non-pariel 103, Nu-core, Nu-pariel) are commercially available in sizes from 35 to 40 mesh to 18 to 14 mesh. Particles of microcrystalline cellulose are preferred pharmaceutical carrier particles. The skilled artisan knows other pellets or spheres useful as pharmaceutical carrier particles.

The microparticles of the drug or pharmacologically active substance of the present invention are obtained by removing a sublimable carrier from a solid solution of the drug in the sublimable carrier. The drug or pharmaceutically active substance can be present with the sublimable carrier in the solid solution as discrete molecules, or it can be present in aggregates of a few hundred, a few thousand, or more molecules. The drug need only be dispersed on a sufficiently small scale so that sufficiently small, discrete microparticles are ultimately obtained. Preferably, the drug or pharmacologically active substance in the solid solution is dissolved in the sublimable carrier.

Sublimable carriers useful in the practice of the present invention form solid solutions with the drug at an easily accessible temperature and can be removed from the solid solution without heating the solid solution to a temperature above the melting point of the solid solution, for example by sublimation. Sublimable carriers have a measurable vapor pressure below their melting point. Preferred sublimable carriers have a vapor pressure of at least about 10 Pascal, more preferably at least about 50 Pascal at about 10° or more below their normal melting points. Preferably, the sublimable carrier has a melting point between about −10° C. and about 200° C., more preferably between about 20° C. and about 60° C., most preferably between about 40° C. and about 50° C. Preferably, the sublimable carrier is a substance that is classified by the United States Food and Drug Administration as generally recognized as safe (i.e., GRAS). Examples of suitable sublimable carriers include menthol, thymol, camphor, t-butanol, trichloro-t-butanol, imidazole, coumarin, acetic acid (glacial), dimethylsulfone, urea, vanillin, camphene, salicylamide, and 2-aminopyridine. Menthol is a particularly preferred sublimable carrier.

The solid solutions of the present invention can exist as a true homogeneous crystalline phase of the interstitial or substitutional type, composed of distinct chemical species occupying the lattice points at random, or they can be a dispersion of discrete molecules or aggregates of molecules in the sublimable carrier.

The solid solutions can be made by combining a drug with molten sublimable carrier, then cooling the combination to below the melting point of the solid solution. The solid solutions can also be formed by combining drug and sublimable carrier in an organic solvent and evaporating the organic solvent to obtain a solid solution of drug in sublimable carrier. Ethanol is an example of a preferred organic solvent that can be used in the practice of the present invention.

The solid solution can also include a compound or polymer that forms a dispersion with the drug.

In a preferred embodiment, the solid solution is formed on the surface of at least one pharmaceutical carrier particle and preferably a plurality of pharmaceutical carrier particles. For example, a molten combination of drug and carrier can be applied to the surface of a pharmaceutical carrier particle where it is allowed to cool to form the solid solution on the surface of the pharmaceutical carrier particle. A solid solution can also be formed at the surface of a pharmaceutical carrier particle by applying a combination of solvent, drug, and sublimable carrier to at least one, and preferably a plurality of, pharmaceutical carrier particle(s) and evaporating the organic solvent to obtain the solid solution on the surface of the pharmaceutical carrier particle.

Application to the pharmaceutical carrier particles can be by any particle coating technique known in the art, for example using fluidized bed equipment or a spray coater. When used, organic solvent is removed after application by exposing the coated carrier particles to vacuum or a stream of heated or non-heated air using particle handling equipment well known in the art.

When no solvent is used, application is at a temperature above the melting point of the sublimable carrier. When drug and sublimable carrier are combined with solvent, application is at a temperature such that drug and sublimable carrier remain in solution in the solvent.

The microparticles of the present invention are formed by removal of sublimable carrier from a solid solution, made as described above, at a temperature below the melting point of the solid solution. The solid solution must be kept at a temperature below its melting point to preserve the solid solution during the process of removing the sublimable carrier. The sublimable carrier can be removed from the solid solution by, for example, treating the solid solution, deposited on a pharmaceutical carrier particle where applicable, in a stream of air, preferably heated air, in, for example, a fluidized bed drier.

In those embodiments in which the solid solution is coated on the surface of a pharmaceutical carrier particle, the sublimable carrier can be removed by exposing the coated particles to heat, vacuum, heat and vacuum, or to a stream of heated or non-heated air, for example in a fluidized bed dryer. Exposing coated pharmaceutical carrier particles to a stream of air (heated or not) in a fluidized bed dryer is a preferred means of removing sublimable carrier from solid solution coated on pharmaceutical carrier particles in order to form the microparticles of the present invention on the surface of the carrier particles.

Removal of sublimable carrier from the solid solution, whether coated on a pharmaceutical carrier particle or not, results in formation of the microparticles of the present invention.

In another embodiment of the present invention, the microparticles of drug or the pharmaceutical carrier particles bearing microparticles of a drug are formulated into pharmaceutical compositions that can be made into dosage forms, in particular oral solid dosage forms such as capsules and compressed tablets, as are well known in the art.

Compressed tablets are formulated from pharmaceutical compositions containing the microparticles of the pharmacologically active substance or drug, or using pharmaceutical carrier particles bearing such microparticles, and pharmacologically inert (pharmaceutically acceptable) additives or excipients.

For making a tablet, it will typically be desirable to include one or more benign pharmaceutical excipients in the pharmaceutical composition. The pharmaceutical composition of the present invention may contain one or more diluents added to make the tablet larger and, hence, easier for the patient and caregiver to handle. Common diluents are microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Binders also may be included in tablet formulations to help hold the tablet together after compression. Some typical binders are acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The tablet may further include a disintegrant to accelerate disintegration of the tablet in the patient's stomach. Disintegrants include alginic acid, carboxymethyl cellulose calcium, carboxymethylcellulose sodium, colloidal silicon dioxide, croscarmellose sodium (e.g. Ac-Di-Sol®, Primellose®), crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

A pharmaceutical composition for making compressed tablets may further include glidants, lubricants, flavorings, colorants and other commonly used excipients.

Pharmaceutical carrier particles bearing microparticles of a drug made in accordance with the present invention have excellent bulk flow properties and can be used directly, alone or in combination with carrier particles that do not carry a drug, to make capsule dosage forms. If necessary, diluents such as lactose, mannitol, calcium carbonate, and magnesium carbonate, to mention just a few, can be formulated with the microparticle-bearing pharmaceutical carrier particles when making capsules Liquid oral pharmaceutical compositions of the present invention comprise microparticles or microparticle-bearing pharmaceutical carrier particles and a liquid carrier such as water, vegetable oil, alcohol, polyethylene glycol, propylene glycol or glycerin, most preferably water.

Liquid oral pharmaceutical compositions may contain emulsifying agents to disperse uniformly throughout the composition the active ingredient, drug delivery vehicle, or excipient having low solubility in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid oral pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

The liquid oral pharmaceutical composition also may contain sweetening agents, such as sorbitol, saccharin, sodium saccharin, sucrose, aspartame, fructose, mannitol and invert sugar; preservatives and chelating agents such as alcohol, sodium benzoate, butylated hydroxy toluene, butylated hydroxyanisole and ethylenediamine tetraacetic acid; and buffers such as guconic acid, lactic acid, citric acid or acetic acid, sodium gluconate, sodium lactate, sodium citrate or sodium acetate.

The present invention is further illustrated with the following examples.

Example 1

Solubility of Selected Drugs in Menthol

The following general procedure was repeated with several drugs with menthol carrier.

Menthol (10 grams) was melted on a stirring hot plate with magnetic stirring, then heated to the desired temperature indicated in Table 1. The desired drug was added in small increments (0.1 grams) and stirred to obtain a clear solution. The desired drug was added in increments until no more drug dissolved in the menthol. The weight of material added to the menthol melt that still gave a clear solution was taken as the solubility of the active drug at the indicated temperature. The results are given in Table 1.

TABLE 1

Solubility of selected active drug substances in menthol

| Active drug substance | temperature (° C.) | Solubility (% w/w) |
| --- | --- | --- |
| Azithromycin | 63 | 40.0 |
| Cyclosporin | 55 | 39.2 |
| Diazepam | 43 | 5.7 |
| Fenofibrate | 60 | 37.5 |
| Itraconazole | 61 | 1.0 |
| Oxybutynin | 60 | 9.1 |
| Risperidone | 70 | 8.3 |
| Salicylic acid | 43 | 16.0 |
| Simvastatin | 63 | 30.0 |

Example 2

Improvement of the Dissolution of Fenofibrate by "Menthol Micronization"

Menthol (50 grams) was heated in a jacketed reactor to 60° C. After melting, the melt was stirred at 100 rpm. Fenofibrate (25 grams) was added and the mixture stirred at 100 rpm and 60° C. until full dissolution was achieved. Microcrystalline cellulose (Avicel ph 102, 55 grams) was added to the melt and the mixture was stirred for 30 minutes. The heat source was then removed and the mass allowed to cool to room temperature with the stirring continued at 100 rpm for a further 30 minutes.

The obtained mass was milled through a 6.35 mm screen in a Quadra Comil mill at 1300 rpm. The milled product was allowed to cool to 25° C. and milled again through 1.4 mm screen to obtain a powder in which the fenofibrate is dissolved in menthol and coated on the microcrystalline cellulose.

The powder was transferred to a fluid bed dryer (Aeromatic model STREA1) where the menthol was removed by drying for three hours at 30-32° C. with the fan at 7-8 $Nm^3$/hr. A powder, 62 grams, was obtained. This powder was an essentially "micronized" fenofibrate deposited on microcrystalline cellulose.

A sample of this powder containing 100 mg of the fenofibrate was tested for dissolution in a USP Apparatus II dissolution tester in 900 ml 0.5% sodium lauryl sulfate (SLS) in water at 37° C. and 100 rpm. The fenofibrate in the dissolution medium was determined by HPLC on an Hypersil® ODS column with UV detection at 286 nm. The results are shown in Table 2. Fenofibrate "micronized" by the menthol method gave 100% dissolution in two hours. An equivalent simple combination of fenofibrate (control, not deposited from menthol) with microcrystalline cellulose gave 40.2% dissolution in 3 hours, while a mechanically micronized fenofibrate raw material mixed with microcrystalline cellulose gave 72.1% dissolution in 3 hours.

TABLE 2

Dissolution of menthol treated fenofibrate

| time (minutes) | % dissolved |
| --- | --- |
| 15 | 44.0 +/− 1.3 |
| 30 | 73.6 +/− 2.9 |
| 60 | 82.3 +/− 0.6 |
| 90 | 93.1 +/− 4.2 |
| 120 | 102.7 +/− 0.2 |
| 180 | 104.9 +/− 0.8 |

Example 3

Improvement of the Dissolution of Oxybutynin Chloride by "Menthol Micronization"

Menthol (80 grams) was melted and oxybutynin chloride (8 grams) and microcrystalline cellulose (89.5 grams) were added and treated as in Example 2 to give a powder of "micronized" oxybutynin chloride on microcrystalline cellulose.

The dissolution of oxybutynin chloride from this powder (a sample of powder containing 100 mg of the active drug) was tested in a USP apparatus II dissolution tester in 100 ml of 50 mM phosphate buffer pH=6.8 at 37° C. and 50 rpm. The oxybutynin content of the dissolution sample was measured by spectrophotometer at 225 tun. The results are given in Table 3. The dissolution reached 79.2% at three hours. An equivalent simple combination of the oxybutynin chloride raw material with microcrystalline cellulose that was not treated with the "menthol micronization" method gave only 22.1% dissolution in three hours.

TABLE 3

Dissolution of menthol treated oxybutynin

| time (minutes) | % dissolved |
| --- | --- |
| 30 | 21.5 +/− 0.4 |
| 90 | 59.7 +/− 1.2 |
| 180 | 79.2 +/− 1.0 |

Example 4

Improvement of the Dissolution of Risperidone by "Menthol Micronization"

Menthol (50 grams) was melted and risperidone (4.5 grams) and microcrystalline cellulose (62.5 grams) were added and treated according to the procedure in Example 2. A sample of the resulting powder (containing 50 mg of risperidone) was tested in a USP apparatus II dissolution tester using 900 ml of water at 37° C. and 100 rpm. The concentration of risperidone in the dissolution samples was measured using a spectrophotometer at 240 nm.

The results of the dissolution of the "menthol micronized" powder and of the control simple combination of risperidone and microcrystalline cellulose (not treated with menthol) are shown in Table 4. The menthol deposited risperidone gave 100% dissolution in 30 minutes, whereas the control mixture gave 31.9% in thirty minutes and 63.7% in three hours.

TABLE 4

Dissolution of menthol treated risperidone vs. control

| time (minutes) | % dissolved test | % dissolved control |
|---|---|---|
| 15 | 69.3 +/− 0.5 | 17.5 +/− 2.6 |
| 30 | 99.9 +/− 1.0 | 31.9 +/− 3.5 |
| 60 | 102.3 +/− 0.8 | 41.7 +/− 5.6 |
| 90 | 102.8 +/− 1.2 | 48.2 +/− 8.3 |
| 120 |  | 53.2 +/− 11.1 |
| 180 |  | 63.7 +/− 8.3 |

Example 5

Improvement of the Dissolution of Cyclosporin by "Menthol Micronization"

Menthol (80 grams) was melted and cyclosporin (20 grams) and microcrystalline cellulose (100 grams) were added and treated as in Example 2. A sample of this powder (containing 10 mg of "menthol micronized" cyclosporin) was tested for dissolution in 900 ml water in a USP apparatus II dissolution unit at 37° C. and 100 rpm. The cyclosporin content of the dissolution samples was determined spectrophotometrically at 215 nm. The dissolution of the menthol deposited material and of a control mixture of cyclosporin and microcrystalline cellulose (not deposited from menthol) are presented in Table 5. The cyclosporin dissolution from the powder having cyclosporin deposited from menthol was about twice that of the control (simple combination), and the maximum dissolution was achieved in shorter time.

TABLE 5

Dissolution of menthol treated cyclosporin vs. control

| time (minutes) | % dissolved test | % dissolved control |
|---|---|---|
| 30 | 9.2 +/− 0.3 | 0.1 +/− 0.0 |
| 60 | 11.9 +/− 0.3 | 1.3 +/− 0.5 |
| 90 | 13.1 +/− 0.5 | 3.1 +/− 0.2 |
| 120 | 13.3 +/− 0.3 | 5.1 +/− 0.2 |
| 180 | 14.3 +/− 0.8 | 7.1 +/− 0.3 |

Example 6

Comparative

Attempted Improvement in Itraconazole Dissolution by "Menthol Micronization"

Menthol (92 grams) was melted as in Example 2. Itraconazole (3.6 grams) was added and mixed well in the melt. A solution was not formed because itraconazole has a solubility of only 1% in menthol at 60° C. (see Table 1). To the suspension of itraconazole in menthol was added microcrystalline cellulose (90 grams) and the mixture treated as in Example 2. The dissolution of the itraconazole was measured from a powder sample containing 100 mg of the drug in 900 ml of 0.1N HCl in a USP apparatus II dissolution tester at 37° C. and 100 rpm. The dissolved itraconazole was measured spectrophotometrically at 251 nm. The results of the dissolution are shown in Table 6. The dissolution was about 8% at 30 minutes and the same at three hours. A control simple mixture of itraconazole and microcrystalline cellulose (not deposited from menthol) gave essentially the same results (7.8% in three hours).

TABLE 6

Dissolution of menthol treated itraconazole

| time (minutes) | % dissolved |
|---|---|
| 30 | 8.8 +/− 0.4 |
| 90 | 8.0 +/− 0.6 |
| 180 | 8.1 +/− 0.1 |

REFERENCES (1) Nielsen, L. S. *Improved peroral bioavailability of mebendazole in rabbits by administration of various N-alkoxycarbonyl derivatives of mebendazole, Int. J. Pharm.* 104, 175-179 (1994)

(2) Chan, O. H. et. al. *Evaluation of a targeted prodrug strategy to enhance oral absorption of poorly water soluble compounds, Pharm. Res.* 15, 1012-1018 (1998)

(3) Fleisher, D. et. al. *Improved oral drug delivery: Solubility limitations overcome by the use of prodrugs, Adv. Drug Deliv. Rev.* 19, 115-130 (1996)

(4) Abang, A. M. *The clinical pharmacology of topoisomerase I inhibitors, Semin. Hematol.* 35 Suppl 4, 13-21 (1998)

(5) Merisko-Liversidge, E., *Formulation and antitumor activity evaluation of nanocrystalline suspensions of poorly soluble anticancer drugs, Pharm. Res.* 13, 272-278 (1996);

(6) Liversidge, G. G., *Particle size reduction for improvement of oral bioavailability of hydrophobic drugs: I. Absolute oral bioavailability of nanocrystalline danazol in beagle dogs, Int. J. Pharm.,* 125, 91-97 (1995)

(7) Muller, R. H., et. al. *Nanosuspensions for the formulation of poorly soluble drugs. I. Preparation by a size reduction technique, Int. J. Pharm.* 160, 229-237 (1998)

(8) Muller, R. H. et. al., *Increase of solubility of poorly soluble drugs by transfer to DissoCubes™ using high pressure homogenization, Proc. Control. Release Soc.* 1999, 112-113, (9) U.S. Pat. No. 6,346,533 to Cha et. al

(10) Morita, T. et. al. *Formation and isolation of spherical fine protein microparticles through lyophilization of protein-poly(ethylene glycol) aqueous mixtures, Pharm. Res.* 17, 1367-1373 (2000)

(11) Tesconi, M. S., *Freeze drying above room temperature, J. Pharm. Sci.* 88, 501-506 (1999)

(12) Ni, N. et. al. *Use of pure butanol as a solvent for freeze drying: a case study, Int. J. Pharm.* 226, 39-46 (2001)

(13a) U.S. Pat. No. 3,089,818 assigned to Baxter laboratories

(13) U.S. Pat. No. 4,900,775 to Smith et. al

(14) Wenz, G. *An overview of host-guest chemistry and its application to nonsteroidal anti-inflammatory drugs, Clin. Drug Invest.* 19 (suppl 2), 21-25 (2000)

(15) Cappello, B., *Solubilization of tropicamide by hydroxypropyl-β-cyclodextrin and water soluble polymers: In vitro/in vivo studies, Int. J. Pharm.* 213, 75-81 (2001)

(16) Sekiguchi et, al. *Chem Pharm. Bull.* 9, 866-872 (1961)

(17) Chiou et. al. *J. Pharm. Sci.* 60, 1281-1302 (1971)

(18) Fernandez, M. et. al., *Characterization of solid dispersions of piroxicam/polyethylene glycol 4000, Int. J. Pharm.* 84, 197-202 (1992)

(19) Margarit, M. V. et. al., *Physical characteristics and dissolution kinetics of solid dispersions of ketoprofen and polyethylene glycol 6000, Int. J. Pharm.* 108, 101-108 (1994)

(20) Sheen, P. C. et. al., *Formulation of poorly water-soluble drug in solid dispersions to improve bioavailability, Int. J. Pharm.* 118, 221-227 (1995)

(21) Kai, T. et. al., *Oral absorption of poorly soluble drug using solid dispersion technique, Chem. Pharm. Bull.* 44, 568-571 (1996)

(22) Serajuddin, A. T. M., *Solid dispersions of poorly water-soluble drugs: Early promises, subsequent problems, and recent breakthroughs, J. Pharm. Sci.,* 88, 1058-1066 (1999)

(23) Lee, E. J. et. al., *Bioavailability of cyclosporin A dispersed in sodium lauryl sulfate-dextrin based solid microspheres, Int J. Pharm.,* 218, 125-131 (2001)

(24) Kapsi, S. G. et. al. *Processing factors in development of solid solution formulation of itraconazole for enhancement of drug dissolution and bioavailability, Int. J. Pharm.,* 229, 193-203 (2001)

(25) Ho, H. O., *The preparation and characterization of solid dispersions on pellets using a fluidized bed system, Int. J. Pharm.* 139, 223-239 (1996)

(26) U.S. Pat. No. 6,027,747 to Terracol et. al.

(27) Betageri, G. V. et. al. *Enhancement of dissolution of glyburide by solid dispersion and lyophilization techniques, Int. J. Pharm.* 126, 155-160 (1995)

(28) Gupta, M. K. et. al. *Enhanced drug dissolution and bulk properties of solid dispersions granulated with a surface adsorbent, Pharm. Dev. Technol.* 6, 563-572 (2001)

What is claimed is:

1. A drug delivery vehicle comprising at least one pharmaceutical carrier particle bearing on its surface microparticles of a poorly water soluble drug, wherein the microparticles have a mean particle size of about 100 nm to about 10 μm; the pharmaceutical carrier particle is selected from the group consisting of starch particles, microcrystalline starch particles, microcrystalline cellulose particles, lactose particles, and sugar particles; and the drug delivery vehicle is prepared by:
   a) forming a solid solution comprising the poorly water soluble drug and a sublimable carrier; and
   b) removing the sublimable carrier from the solid solution to deposit microparticles of the drug on the surface of the pharmaceutical carrier particle.

2. The drug delivery vehicle of claim 1 wherein the pharmaceutical carrier particle comprises particles of microcrystalline cellulose.

3. A pharmaceutical composition comprising at least one pharmaceutically acceptable excipient and the drug delivery vehicle of claim 1.

4. An oral solid dosage form comprising a pharmaceutical composition according to claim 3.

5. The drug delivery vehicle of claim 1 wherein the ratio of carrier particles to drug is about 2:1 to about 14:1.

6. The drug delivery vehicle of claim 5, wherein the microparticles are obtained without mechanical micronization.

7. The drug delivery vehicle of claim 1, wherein the sublimable carrier is selected from the group consisting of menthol, thymol, camphor, t-butanol, trichloro-t-butanol, imidazole, coumarin, acetic acid (glacial), dimethylsulfone, urea, vanillin, camphene, salicylamide, and 2-aminopyridine.

8. The drug delivery vehicle of claim 1, wherein the drug is selected from the group consisting of itraconazole, bromocriptine, carbamazepine, diazepam, paclitaxel, etoposide, camptothecin, danazole, progesterone, nitrofurantoin, estradiol, estrone, oxfendazole, proquazone, ketoprofen, nifedipine, verapamil, and glyburide.

\* \* \* \* \*